US011406771B2

(12) United States Patent
Smith et al.

(10) Patent No.: US 11,406,771 B2
(45) Date of Patent: Aug. 9, 2022

(54) APPARATUSES AND METHODS FOR DELIVERING POWDERED AGENTS

(71) Applicant: Boston Scientific Scimed, Inc., Maple Grove, MN (US)

(72) Inventors: Amanda Lynn Smith, Brookline, MA (US); Gerald Fredrickson, Westford, MA (US); Dennis Brian Hubbard, Jr., Lancaster, MA (US); Stan Robert Gilbert, Litchfield, NH (US); Caitlyn Emily Bintz, Marlborough, MA (US); Andrew Pic, Ashland, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1159 days.

(21) Appl. No.: 15/865,723

(22) Filed: Jan. 9, 2018

(65) Prior Publication Data
US 2018/0193574 A1 Jul. 12, 2018

Related U.S. Application Data

(60) Provisional application No. 62/444,586, filed on Jan. 10, 2017.

(51) Int. Cl.
*A61M 11/02* (2006.01)
*A61M 13/00* (2006.01)
(Continued)

(52) U.S. Cl.
CPC .......... *A61M 11/02* (2013.01); *A61M 13/00* (2013.01); *A61B 2017/00893* (2013.01);
(Continued)

(58) Field of Classification Search
CPC .................. A61M 11/06; A61M 13/00; A61M 15/0005; A61M 15/0008; A61M 15/0065;
(Continued)

(56) References Cited

U.S. PATENT DOCUMENTS 471,854 A 3/1892 Howard
881,238 A 3/1908 Hasbrouck
(Continued)

FOREIGN PATENT DOCUMENTS

CN 101401956 B 11/2012
DE 60215438 T2 8/2007
(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Scott J Medway
*Assistant Examiner* — John A Doubrava
(74) *Attorney, Agent, or Firm* — Bookoff McAndrews, PLLC

(57) ABSTRACT

In one aspect of the present disclosure, an apparatus for delivering a powdered agent into a subject's body may include a powder chamber housing the powdered agent. The apparatus also may include a chassis in fluid connection with the powder chamber. The chassis may include a first passage for receiving a pressurized gas, a second passage for receiving the powdered agent from the powder chamber, and a junction in fluid communication with the first passage and the second passage. At least a first portion of the pressurized gas is introduced into the powdered agent at the junction to fluidize the powdered agent.

18 Claims, 5 Drawing Sheets

(51) Int. Cl.
*A61B 17/00* (2006.01)
*A61M 15/00* (2006.01)
*A61M 11/06* (2006.01)
*A61M 16/12* (2006.01)

(52) U.S. Cl.
CPC ......... *A61M 11/06* (2013.01); *A61M 15/0005* (2014.02); *A61M 15/0008* (2014.02); *A61M 15/0065* (2013.01); *A61M 16/127* (2014.02); *A61M 2202/064* (2013.01); *A61M 2205/8218* (2013.01)

(58) Field of Classification Search
CPC ........ A61M 16/127; A61M 2205/8218; A61B 2017/00893; A61B 2202/064
See application file for complete search history.

(56) References Cited

U.S. PATENT DOCUMENTS

| | | |
|---|---|---|
| 1,145,520 A | 7/1915 | Smith |
| 1,599,959 A | 9/1926 | Buheiji |
| 1,732,566 A | 10/1929 | McKendrick |
| 2,151,418 A | 3/1939 | Bolté |
| 2,185,927 A | 6/1940 | Shelanski |
| 2,478,715 A | 8/1949 | Schmitt |
| 2,623,519 A | 12/1952 | Cohen |
| 3,044,908 A | 7/1962 | Baldi |
| 3,237,805 A | 3/1966 | Stogner |
| 3,425,600 A | 2/1969 | Abplanalp |
| 3,485,535 A | 12/1969 | Fabre |
| 3,669,113 A | 6/1972 | Altounyan et al. |
| 3,940,061 A | 2/1976 | Gimple et al. |
| 4,184,258 A | 6/1980 | Barrington et al. |
| 4,427,450 A | 1/1984 | Kostansek |
| 4,457,329 A | 7/1984 | Werley et al. |
| 4,620,847 A | 11/1986 | Shishov et al. |
| 4,678,377 A | 7/1987 | Bouchard |
| 4,806,167 A | 2/1989 | Raythatha |
| 4,824,295 A | 4/1989 | Sharpless |
| 5,215,221 A | 6/1993 | Dirksing |
| 5,231,983 A | 8/1993 | Matson et al. |
| 5,273,531 A | 12/1993 | Knoepfler |
| 5,310,407 A | 5/1994 | Casale |
| 5,312,331 A | 5/1994 | Kneopfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,618,177 A | 4/1997 | Abbott |
| 5,884,621 A | 3/1999 | Matsugi et al. |
| 5,951,531 A | 9/1999 | Ferdman et al. |
| 6,003,512 A | 12/1999 | Gerde |
| 6,261,258 B1 | 7/2001 | Saines |
| 6,484,750 B1 | 11/2002 | Foos et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |
| 6,716,190 B1 | 4/2004 | Glines et al. |
| 6,722,363 B1 | 4/2004 | Von Schuckmann |
| 6,799,571 B1 | 10/2004 | Hughes et al. |
| 6,945,953 B2 | 9/2005 | Wright |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,465,287 B2 | 12/2008 | James |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,834,411 B2 | 9/2014 | Shay et al. |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Mackal |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,806,853 B2 | 10/2020 | Gittard |
| 10,850,814 B2 | 12/2020 | Fawcett |
| 10,994,818 B2 | 5/2021 | Hernandez |
| 2004/0107963 A1 | 6/2004 | Finlay et al. |
| 2004/0249359 A1 | 12/2004 | Palasis et al. |
| 2005/0121025 A1 | 6/2005 | Gamard et al. |
| 2005/0147656 A1 | 7/2005 | McCarthy et al. |
| 2005/0205087 A1 | 9/2005 | Kablik et al. |
| 2005/0220721 A1 | 10/2005 | Kablik et al. |
| 2006/0004314 A1 | 1/2006 | McCarthy et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0160543 A1 | 7/2007 | Moller |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0287907 A1 | 11/2008 | Gregory et al. |

(56) References Cited

U.S. PATENT DOCUMENTS

| | | | |
|---|---|---|---|
| 2009/0013994 A1* | 1/2009 | Jones | A61M 15/002 128/200.23 |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0274726 A1 | 11/2011 | Guo et al. | |
| 2011/0308516 A1 | 12/2011 | Price et al. | |
| 2013/0218072 A1* | 8/2013 | Kubo | A61M 13/00 604/58 |
| 2014/0018729 A1 | 1/2014 | Foster et al. | |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1* | 10/2017 | Lee | B05B 7/1486 |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |
| 2019/0232030 A1 | 8/2019 | Pic et al. | |
| 2021/0024187 A1 | 1/2021 | Fawcett et al. | |
| 2021/0069485 A1 | 3/2021 | Rogier | |

FOREIGN PATENT DOCUMENTS

| | | | |
|---|---|---|---|
| EP | 2 689 796 A1 | 1/2014 | |
| EP | 3052168 B1 | 11/2019 | |
| JP | H07118305 A | 5/1995 | |
| JP | 200278774 A | 3/2002 | |
| JP | 2006507876 A | 3/2006 | |
| JP | 201119970 A | 2/2011 | |
| JP | 201162545 A | 3/2011 | |
| JP | 2012143502 A | 8/2012 | |
| JP | 2012152420 A | 8/2012 | |
| WO | 03013552 A1 | 2/2003 | |
| WO | 2004066806 A2 | 8/2004 | |
| WO | 2005062896 A2 | 7/2005 | |
| WO | 2006071649 A2 | 7/2006 | |
| WO | 2006088912 A2 | 8/2006 | |
| WO | 2008033462 A2 | 3/2008 | |
| WO | 2009061409 A1 | 5/2009 | |
| WO | 2015050814 A1 | 4/2015 | |
| WO | 2016048006 A1 | 3/2016 | |
| WO | 2018157772 A1 | 9/2018 | |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, COOK, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

Japanese Office Action dated Jan. 11, 2022 in counterpart Japanese Patent Application 2019-536821 (5 pages, in Japanese).

\* cited by examiner

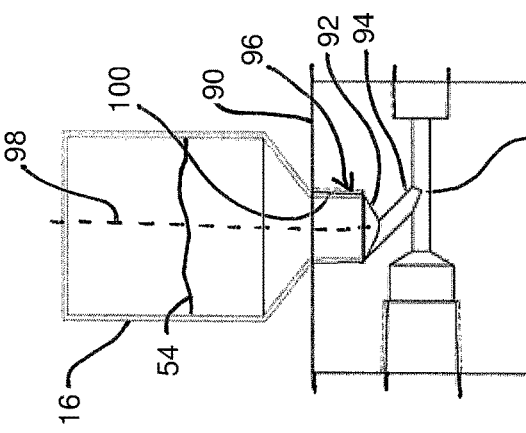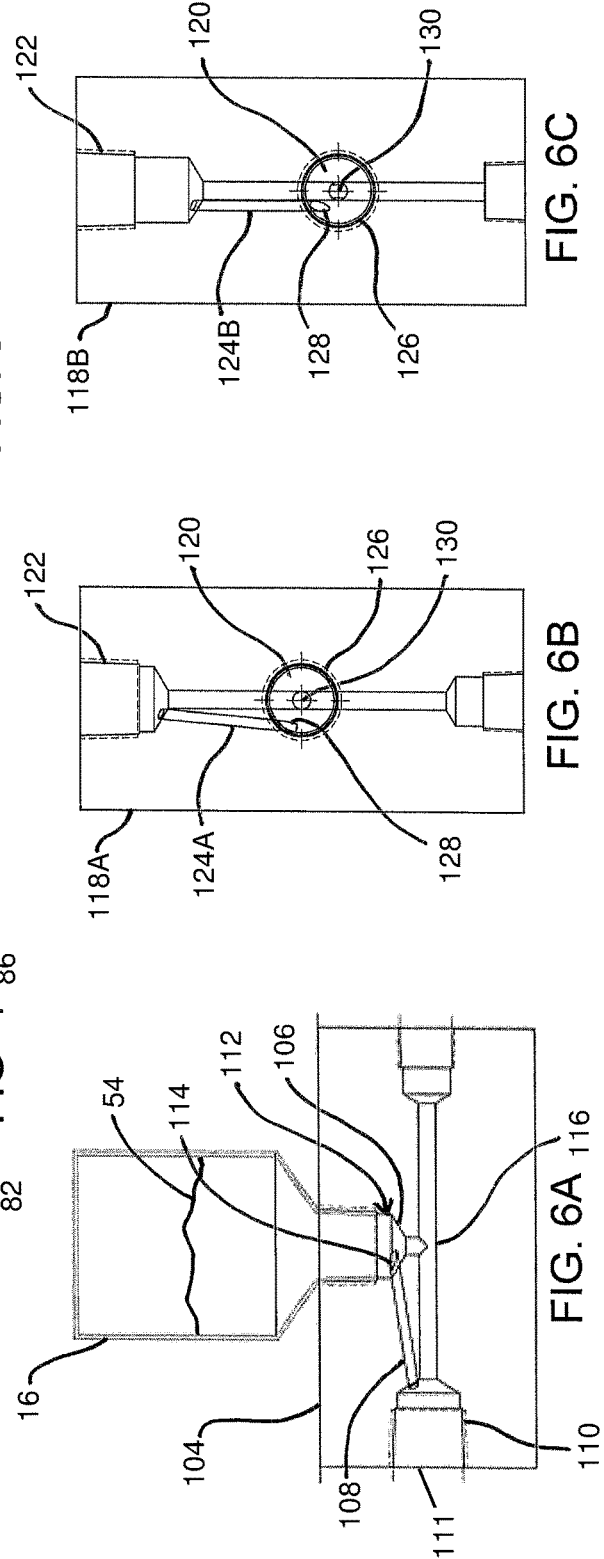

APPARATUSES AND METHODS FOR DELIVERING POWDERED AGENTS

CROSS-REFERENCE TO RELATED APPLICATION(S)

This patent application claims the benefit under 35 U.S.C. § 119 to U.S. Provisional Application No. 62/444,586, filed on Jan. 10, 2017, the entirety of which is incorporated herein by reference.

TECHNICAL FIELD

Various aspects of the present disclosure relate generally to apparatuses and methods for delivering powdered agents. More specifically, the present disclosure relates to apparatuses and methods for the endoscopic delivery of hemostatic powders

BACKGROUND

When bleeding occurs in a subject's body during a medical procedure, a user performing the procedure may seek ways in which to reduce or to eliminate the bleeding. One way to manage bleeding is by applying a hemostatic powder at a site of the bleeding. Where the medical procedure being performed is an endoscopic procedure, applying the hemostatic powder at the site may entail delivering the powder to the site using a catheter. Ensuring that the hemostatic powder can be properly delivered to the site through the catheter may lead to improved outcomes.

SUMMARY

Aspects of the present disclosure relate to, among other things, apparatuses and methods for delivering powdered agents. Each of the aspects disclosed herein may include one or more of the features described in connection with any of the other disclosed aspects.

In one aspect of the present disclosure, an apparatus for delivering a powdered agent into a subject's body may include a powder chamber housing the powdered agent. The apparatus also may include a chassis in fluid connection with the powder chamber. The chassis may include a first passage for receiving a pressurized gas, a second passage for receiving the powdered agent from the powder chamber, and a junction in fluid communication with the first passage and the second passage. At least a first portion of the pressurized gas is introduced into the powdered agent at the junction to fluidize the powdered agent. The chassis also may include a third passage in fluid communication with the junction. The third passage may receive the fluidized powdered agent from the junction for exiting the chassis. The chassis also my include a fourth passage in fluid communication with the first passage and the second passage for directing a second portion of the pressurized gas from the first passage into the second passage to move the powdered agent in the second passage before the powdered agent is directed into the junction from the second passage.

Aspects of the apparatus may include one or more of the features below. The powder chamber may be positioned above the chassis, such that gravity assists movement of the powdered agent out of the powder chamber and into the second passage. The first passage, the junction, and the third passage may be substantially aligned. A central longitudinal axis of the second passage may be substantially perpendicular to a central longitudinal axis of at least one of the first passage and the third passage. An opening may be formed in a wall of the second passage where the fourth passage meets the second passage. The second passage may include a tapered region, and the opening may be formed on the tapered region. An angle of the fourth passage relative to the second passage may cause the second portion of the pressurized gas to be emitted tangentially relative to a wall of the second passage to create a vortex of the pressurized gas and the powdered agent in the second passage.

In another aspect of the present disclosure, an apparatus for delivering a powdered agent into a body may include a mixing chamber for coupling to a source of pressurized gas, a source of the powdered agent, and a catheter. The mixing chamber may include a first passage for receiving the pressurized gas from the pressurized gas source, a second passage for receiving the powdered agent from the source of the powdered agent, and a junction downstream from the first passage and the second passage. The junction may be configured to introduce the pressurized gas from the first passage into the powdered agent from the second passage to fluidize the powdered agent. The chassis also may include a third passage downstream from the junction. The third passage may be configured to receive the fluidized powdered agent from the junction and direct the fluidized powdered agent into the catheter. The chassis also may include a fourth passage branching from the first passage and leading directly to the second passage. The fourth passage may be configured to direct a portion of the pressurized gas from the first passage into the second passage.

Aspects of the apparatus may include one or more of the features below. The second passage may be positioned above the junction, such that gravity assists with moving the agitated powdered agent from the second passage into the junction. The first passage, the junction, and the third passage may be substantially aligned. A central longitudinal axis of the second passage may be substantially perpendicular to a central longitudinal axis of at least one of the first passage and the third passage. An opening may be formed in a wall of the second passage where the fourth passage meets the second passage. The second passage may include a tapered region, and the opening may be formed on the tapered region. An angle of the fourth passage relative to the second passage may cause the portion of the pressurized gas to be emitted substantially tangentially relative to a wall of the second passage for creating a vortex of the pressurized gas and the powdered agent in the second passage.

In another aspect of the present disclosure, a method for providing a powdered agent to a treatment site in a body may include delivering the powdered agent to the treatment site using a powder chamber housing the powdered agent, a catheter, and a chassis coupled to the powder chamber and the catheter. Delivering the powdered agent may include directing a first flow of pressurized gas into the powdered agent. The delivering step also may include fluidizing the agitated powdered agent by directing a second flow of pressurized gas, separate from the first flow of pressurized gas, into the agitated powdered agent. The delivering step also may include directing the fluidized powdered agent into the catheter. The delivering step also may include emitting the fluidized powdered agent from a distal end of the catheter to the treatment site.

Aspects of the method may include one or more of the features below. Directing the first flow of pressurized gas into the powdered agent to form a vortex of the pressurized gas and the powdered agent. Having the first flow of pressurized gas and the second flow of pressurized gas branch off from the same flow of pressurized gas. Directing a third flow of pressurized gas around the powdered agent to bypass the powdered agent, wherein the bypassing maintains pressure within the catheter when the powdered agent forms a clog in the chassis. At least one of (i) causing blood at the site to coagulate through interaction between the powdered agent and the blood, and (ii) forming a pseudoclot at the site through interaction between the powdered agent and one or more fluids at the site. At least one of (i) agitating the powdered agent using a rotating auger housed in at least one of the chassis and the powder chamber, (ii) agitating the powdered agent using a vibrating wire housed in the chassis, (iii) agitating the powdered agent using a vibrating ring mounted on the powder chamber, and (iv) expelling the powdered agent from the powder chamber by collapsing at least a portion of the powder chamber.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

FIGS. 2-11 show mixing chambers, in accordance with aspects of the present disclosure.

DETAILED DESCRIPTION

The present disclosure is drawn generally to apparatuses and methods for delivering powdered agents, and more specifically to apparatuses and methods for the endoscopic delivery of hemostatic powders. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing an instrument into a subject. By contrast, the term "proximal" refers to a portion closest to the user when placing the instrument into the subject. Though the following description refers to "endoscope" or "endoscopy," the principles/aspects described herein may be used with any suitable introduction sheath or device, even if such sheath or device fails to include one or more features typically associated with "endoscopes." It may be understood that both the foregoing general description and the following detailed description are exemplary and explanatory only and are not restrictive of the features claimed. Further, as used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

The terms "substantially," "approximately" and "about" refer to a variation of plus or minus ten percent with respect to a stated value.

Figure 1:
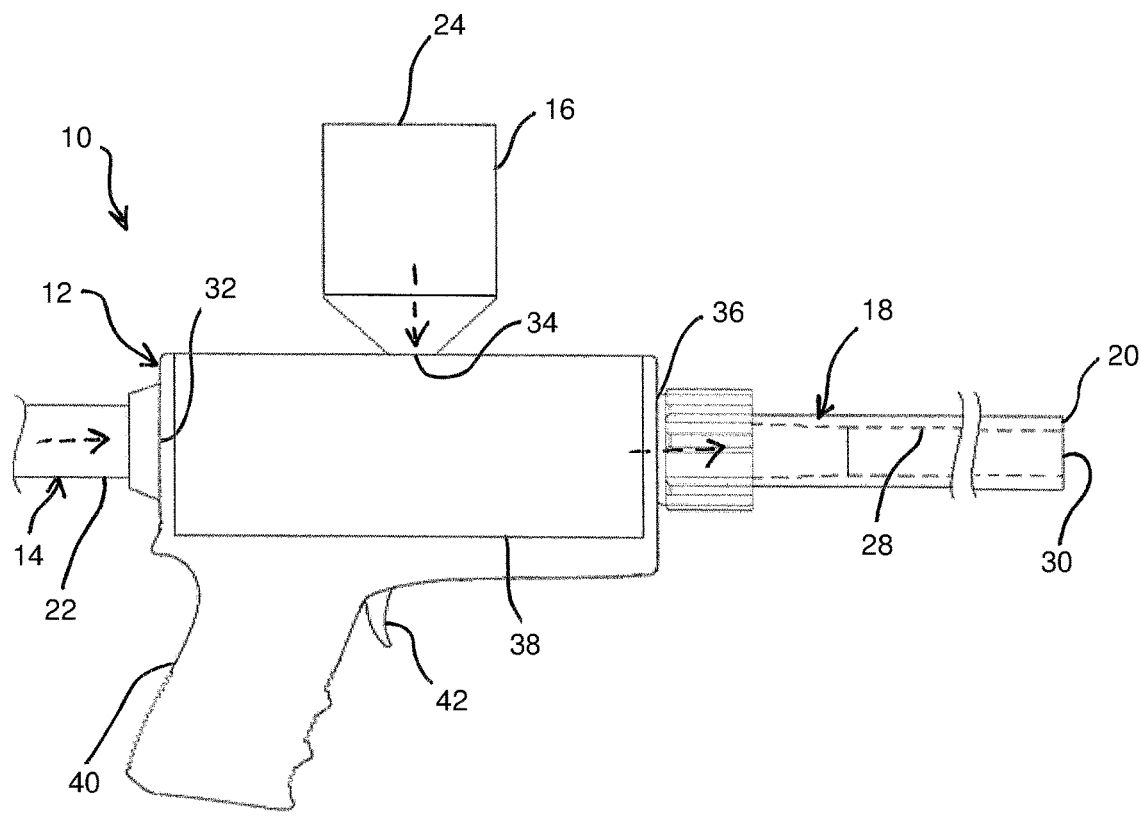
FIG. 1 shows an apparatus for delivering powdered agents, in accordance with aspects of the present disclosure.

FIG. 1 shows one example of an apparatus 10 for delivering powdered agents, in accordance with aspects of the present disclosure. Apparatus 10 may include, for example, a chassis 12, a gas supply 14 for supplying a pressurized gas to chassis 12, a powder chamber 16 for supplying a powdered agent 54 (FIG. 2) to chassis 12, and/or a catheter 18 for receiving a fluidized powdered agent from chassis 12. The fluidized powdered agent may include a mixture of the pressurized gas and the powdered agent. In one example, the pressurized gas may include air, and the powdered agent may include a hemostatic powder. The hemostatic powder may include, for example, particulate material that can stanch bleeding by initiating a coagulation cascade to clot a bleed, and/or a particulate material that can form a pseudoclot upon coming into contact with blood due to hydrophilic properties of the powder.

During use with a subject (e.g., a patient), chassis 12, gas supply 14, and powder chamber 16 may remain outside of the subject, while catheter 18 may enter into the subject through, for example, an endoscope or other introducer sheath (not shown). In one contemplated use, catheter 18 may be inserted through the endoscope or sheath to position a distal end 20 of catheter 18 at or near a site of bleeding in the subject. The fluidized powdered agent may be emitted from the distal end 20 to the site to reduce or stop the bleeding.

Gas supply 14 may include, for example, a gas line 22. Gas line 22 may include a flexible length of tubing. A proximal end of gas line 22 may be coupled to a pressurized gas source (not shown), and a distal end of gas line 22 may be coupled to chassis 12, thereby creating a path for the pressurized gas to flow from the pressurized gas source to chassis 12. The pressurized gas source may include, for example, a pump device, a wall access in a hospital room, a canister, a manually-operated pump, a foot pedal-operated pump, and/or any other suitable pressurized gas source. Gas line 22 may be fixedly attached or removably attached to chassis 12 and/or the pressurized gas source.

Figure 2:
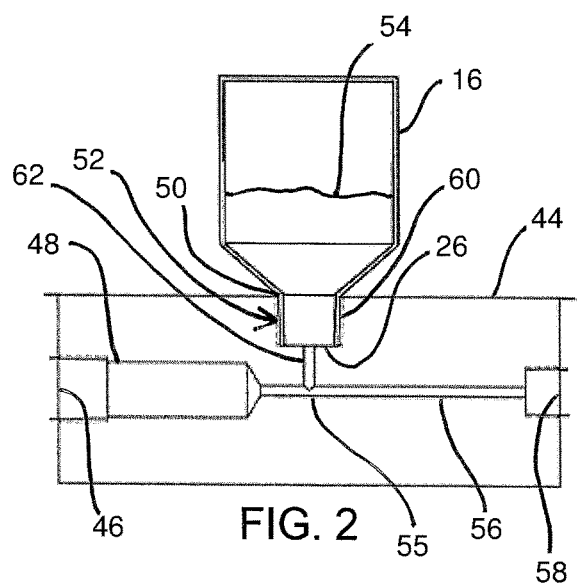

Powder chamber 16 may include any suitable receptacle for holding powdered agent 54. Powder chamber 16 may include, for example, a substantially rigid vessel, such as a bottle. Alternatively, powder chamber 16 may include a substantially flexible vessel, such as a bag. Powder chamber 16 may have a closed end 24 and an open end 26 (FIG. 2). Powdered agent 54 may pass through open end 26 on its way into chassis 12.

Powder chamber 16 may be fixedly attached or removably attached to chassis 12. Where powder chamber 16 is fixedly attached to chassis 12, reloading chassis 12 with powdered agent 54 may include removing a cap, cover, or the like from powder chamber 16, and pouring powdered agent 54 into powder chamber 16. Where powder chamber 16 is removably attached to chassis 12, reloading chassis 12 with powdered agent 54 may include removing an empty powder chamber 16 from chassis 12, and coupling a full powder chamber 16 to chassis 12.

Catheter 18 may include a tubular length of medical grade material, and may have a proximal end with a proximal opening (not visible) and distal end 20 with a distal opening 30 The proximal end of catheter 18 may be coupled to chassis 12. Catheter 18 may include a lumen 28 extending therethrough from the proximal opening to distal opening 30. Fluidized powdered agent 54 from chassis 12 may flow through lumen 28 on its way to being emitted from distal opening 30. Catheter 18 may be sufficiently rigid to maintain its shape when inserted into the subject's body. Alternatively, catheter 18 may be sufficiently flexible to bend and conform to passages in the subject's body. Catheter 18 may be fixedly or removably attached to chassis 12.

Chassis 12 may include an inlet or port 32 to which gas line 22 may be coupled, an inlet or port 34 to which powder chamber 16 may be coupled, and an outlet or port 36 to which catheter 18 may be coupled. Chassis 12 may include a mixing chamber 38 that may be in fluid communication with which inlet 32, inlet 34, and outlet 36. During use, the pressurized gas from gas line 22 may enter mixing chamber 38 via inlet 32, and powdered agent 54 may enter mixing chamber 38 via inlet 34. The pressurized gas and powdered agent 54 may mix in mixing chamber 38, producing fluidized powdered agent 54 that then exits from mixing chamber 38 and enters catheter 18 via outlet 36. Powdered agent 54 may be fluidized in that the pressurized gas may be introduced into powdered agent 54, resulting in the formation of a part-gas and part-solid medium having properties and characteristics of a fluid, such as a liquid.

Chassis 12 also may include a handle 40 for gripping by the user, and a trigger 42 for managing the flow of fluidized powdered agent 54. For example, trigger 42 may be operatively coupled to one or more valves (not shown) in one or more of inlet 32, inlet 34, mixing chamber 38, and outlet 36, to control the flow of one or more of the pressurized gas, powdered agent, and the fluidized powdered agent.

Mixing chamber 38 may be fixedly attached or removably attached to the rest of chassis 12. The removable attachment may be provided by any suitable mechanical attachment mechanism, such as by snap-fit engagement, friction fit, a latching mechanism, or the like. The removable attachment may allow the user to swap out one mixing chamber for another. FIGS. 2-11 show examples of mixing chambers. It is contemplated that any of the mixing chambers may be used in place of any other mixing chamber, including mixing chamber 38. It also is contemplated that any aspect of any of the mixing chambers may be used in any of the other mixing chambers.

FIG. 2 shows a mixing chamber 44. Mixing chamber 44 may be used in place of mixing chamber 38 in FIG. 1. The same is true for other mixing chambers described below. Mixing chamber 44 may include an opening 46 and a passage 48 for the pressurized gas. Mixing chamber 44 also may include an opening 50 and a passage 52 for powdered agent 54. Passage 48 and passage 52 may meet at a junction 55, where the pressurized gas may be introduced into powdered agent 54, thereby fluidizing powdered agent 54. Mixing chamber 44 also may include a passage 56 and an opening 58 for fluidized powdered agent 54. Any of the openings in mixing chamber 44 may have a circular shape. Any of the passages of mixing chamber 44 may have a circular cross-sectional shape. Other suitable opening shapes/cross-sectional shapes may be used, including, for example, polygonal and irregular shapes. It is contemplated that central longitudinal axes of passages 48 and 56 may be substantially aligned or coaxial. Additionally or alternatively, a central longitudinal axis of passage 52 may be substantially perpendicular to at least one of the central longitudinal axes of passages 48 and 56.

Passage 52 may include portions having different widths or diameters. For example, passage 52 may include a first portion 60 and a second portion 62. First portion 60 may be wider than second portion 62. The width, or diameter, of first portion 60 may be designed to receive open end 26 of powder chamber 16. Second portion 62, including its width or diameter, may be designed to control a rate of flow of powdered agent 54 into junction 55. Powder chamber 16 and passage 52 may be positioned above junction 55 such that gravity may assist with moving powdered agent 54 down from powder chamber 16 and passage 52 into junction 55.

Figure 3:
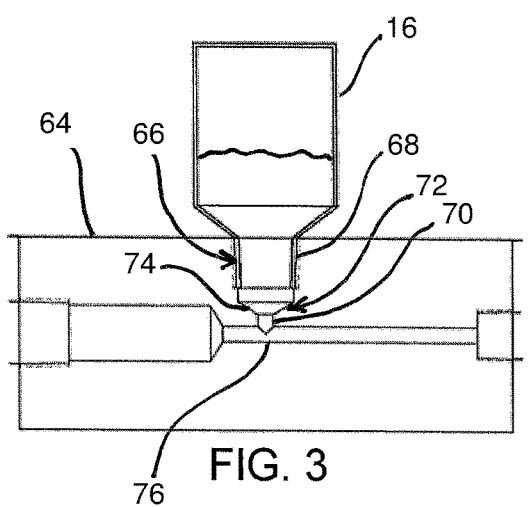

FIG. 3 shows a mixing chamber 64 including a passage 66 having a first portion 68 having a first width, a second portion 70 having a second width smaller than the first width, and a third portion 72. First portion 68 and second portion 70 may be similar to first portion 60 and second portion 62 of mixing chamber 44, respectively, including having constant widths/diameters along their lengths. Third portion 72 may extend between first portion 68 and second portion 70, and may have a varying width or diameter. For example, third portion 72 may include a tapered region 74 having decreasing width or diameter in a direction extending from first portion 68 to second portion 70. Tapered region 74 may act as a funnel to facilitate delivery of powdered agent 54 toward a junction 76. This may reduce or eliminate packing or clogging of powdered agent 54 in passage 66.

FIG. 4 shows another mixing chamber 78. Mixing chamber 78 may include a tapered region 80 similar to tapered region 74 of mixing chamber 64. Mixing chamber 78 may be shorter than mixing chamber 44 and/or mixing chamber 64, as measured along a direction of pressurized gas flow through the mixing chambers. For example, a length of mixing chamber 78 (measured left to right in FIG. 4) may be shorter than a height of mixing chamber 78 (measured up and down in FIG. 4.) Accordingly, a passage 82 for the pressurized fluid, and/or a passage 84 for the fluidized powdered agent 54, may be commensurately shorter. Reducing the passage length(s) may reduce the amount of time powdered agent 54 is in mixing chamber 78, thereby reducing or eliminating packing or clogging in junction 86 and/or passage 84. It is contemplated that a width or diameter of one or more of passage 82, passage 84, and a passage 88 for powdered agent 54, may be widened to further reduce/eliminate clogging.

FIG. 5 shows another mixing chamber 90. Mixing chamber 90 may include a tapered region 92 similar to tapered region 74 of mixing chamber 64. Mixing chamber 90 may be shorter than mixing chamber 44 and/or mixing chamber 64, similar to mixing chamber 78. In mixing chamber 90, a portion 94 of a passage 96 may be angled relative to a central longitudinal axis 98 of another portion 100 of passage 96. In some examples, a central longitudinal axis of portion 94 may form an angle of between approximately 25 degrees and approximately 90 degrees relative to a central longitudinal axis of a junction 102. In one example, the angle may be approximately 45 degrees. Portion 100 may be designed to receive open end 26 of powder chamber 16, and portion 94 may be designed to deliver powdered agent 54 to junction 102. Due to the angle of portion 94, powdered agent 54 may be delivered to junction 102 at a slower rate than if portion 94 was aligned with central longitudinal axis 100. The slower rate may reduce or eliminate packing or clogging of powdered agent 54 at or around junction 102 as powdered agent 54 mixes with the pressurized gas.

FIG. 6A shows another mixing chamber 104. Mixing chamber 104 may include a tapered region 106 similar to tapered region 74 of mixing chamber 64. Mixing chamber 104 also may include a passage 108 connecting a passage 110 for the pressurized gas to a passage 112 for powdered agent 54. Passage 108 may extend alongside passage 110. It is contemplated that passage 108 may be angled relative to passage 110 when viewing mixing chamber 104 from the side view of FIG. 6A. For example, passage 108 may be inclined relative to passage 110, such that passage 108 may extend farther and farther away from passage 110 along a direction of flow of the pressurized gas through passages 108 and 110. An opening 114, where passage 108 meets passage 112, may be positioned at tapered region 106. The pressurized fluid may split into two branches, one branch flowing through passage 108 directly into passage 112, and the other branch flowing through passage 110 toward a junction 116 of passages 110 and 112. Thus, some pressurized gas exits passage 110 between opening 111 upstream in passage 110 and junction 116 where passage 110 meets passage 112 The pressurized fluid that exits in the middle of passage 110 enters passage 108, flows directly into passage 112, upstream of junction 116, and may agitate powdered agent 54 in passage 112 to reduce or eliminate packing or clogging of powdered agent 54. This may facilitate the outflow of powdered agent 54 from powder chamber 16 into junction 116.

FIGS. 6B and 6C show versions of a mixing chamber, identified as mixing chamber 118A in FIG. 6B and mixing chamber 118B in FIG. 6C. Mixing chambers 118A and 118B may be similar to mixing chamber 104. Each of mixing chambers 118A and 118B may include a tapered region 120 of a passage 126 for powdered agent 54, a passage 124A or 124B connecting a passage 122 for the pressurized gas to passage 126, and an opening 128 in passage 126. In one example, mixing chambers 118A and 118B may appear nearly identical to mixing chamber 104 from the side view.

Opening 128 is positioned further from a central longitudinal axis 130 of passage 126 in mixing chamber 118A than in mixing chamber 118B. Passage 124A of mixing chamber 118A may be angled relative to passage 122 when viewing mixing chamber 118A from the top, as shown by FIG. 6B. For example, central longitudinal axes (not shown) of passage 124A and passage 122 are angled relative to each other in the top view of FIG. 6B. The gap between passage 124A and passage 122 may increase along a direction of flow of the pressurized gas through passages 122 and 124A to passage 126. The pressurized gas entering passage 126 may swirl around passage 126, creating a vortex that swirls powdered agent 54 around passage 126. This swirling may reduce or eliminate packing or clogging of powdered agent 54 in passage 112.

Opening 128 is positioned closer to central longitudinal axis 130 of passage 126 in mixing chamber 118B than in mixing chamber 118A. Passage 124B may extend substantially parallel to passage 122 when viewing mixing chamber 118B from the top, as shown by FIG. 6C. For example, central longitudinal axes (not shown) of passage 124B and passage 122 are parallel to each other in the top view of FIG. 6C. The gap between passage 124B and passage 122 may remain substantially constant along a direction of flow of the pressurized gas through passages 122 and 124B to passage 126. The pressurized gas entering passage 126 may agitate powdered agent 54 just prior to powdered agent 54 entering a bottleneck created by the narrower end of tapered section 120. The agitation may be provided by a smaller vortex than the one for FIG. 6B. In either circumstance, the vortex may reduce or eliminate packing or clogging of powdered agent 54 in passage 126. The vortex also may constitute a first fluidization stage, with a second fluidization stage taking place in the junction, resulting in enhanced fluidization of powdered agent 54.

Figure 7:
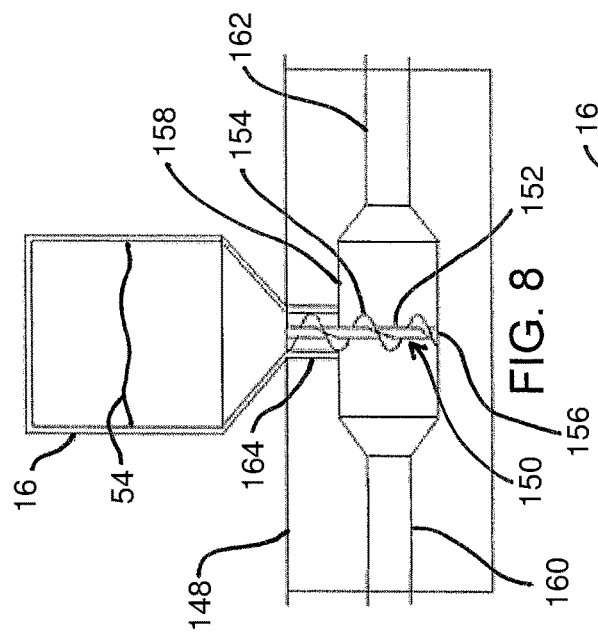

FIG. 7 shows a mixing chamber 132 including an opening 134 and a passage 136 for the pressurized gas, an opening 138 and a passage 140 for powdered agent 54, a junction 142 where the pressurized gas may be introduced into powdered agent 54 to fluidize powdered agent 54, and a passage 144 and an opening 146 for fluidized powdered agent 54. Junction 142 may be enlarged relative to passages 136, 140, and 144, providing a relatively large volume in which powdered agent 54 may be fluidized by the pressurized gas. For example, junction 142 may have a greater cross-sectional width or diameter than one or more of passages 136 and 144. Junction 142 may taper inward at its ends to transition from its relatively larger cross-sectional width or diameter to the cross-sectional width or diameter of each of passages 136 and 144. Gravity may urge powdered agent 54 down from powder chamber 16 into junction 142.

Figure 8:
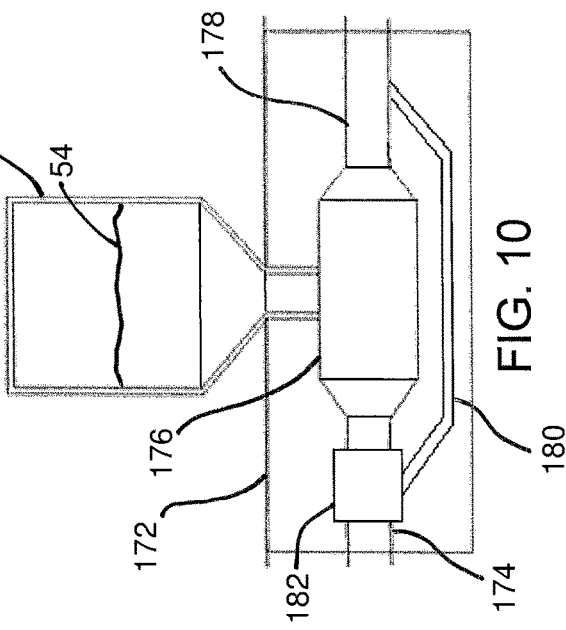

FIG. 8 shows a mixing chamber 148 including an auger 150. Auger 150 may include a shaft 152 and a helical flange 154 extending longitudinally along shaft 152. Shaft 152 may be rotationally coupled to a portion of mixing chamber 148, such as a wall 156 of a junction 158. Shaft 152 may be rotated by an actuator (not shown), such as a manually-operated dial or knob, a motor, a gear assembly, and/or any other suitable actuator. As shaft 152 rotates, helical flange 154 may convey powdered agent 54 from powder chamber 16 into junction 158 via a passage 164. In one example, a diameter or width of auger 150 may be smaller than a diameter or width of passage 164. Radially-outer edge portions of helical flange 154 may contact wall portions defining passage 164. The rate at which powdered agent 54 may be conveyed into junction 158 may be controlled by adjusting a rate of rotation of auger 150. Additionally, auger 150 may help loosen powdered agent 154, thereby reducing or eliminating packing or clogging. The pressurized gas from a passage 160 may enter junction 158 and fluidize powdered agent 54. Fluidized powdered agent 54 may exit junction 158 via a passage 162. It is contemplated that the pressurized gas may impinge on one or more surfaces of auger 150, such as on helical flange 154, to rotate auger 150 either with or without the assistance of a separate actuator.

In one example, shaft 152 may extend substantially perpendicular to junction 158, passage 160, and/or passage 162. For example, a central longitudinal axis of shaft 152 may extend substantially perpendicular to a central longitudinal axis of one or more of junction 158, passage 160, and passage 162. Additionally or alternatively, shaft 152 may be aligned with passage 164. For example, the central longitudinal axis of shaft 152 may be substantially coaxial with or parallel to a central longitudinal axis of passage 164. It is contemplated that auger 150 may be used in any of the other mixing chambers described herein and shown in other figures.

Figure 9:
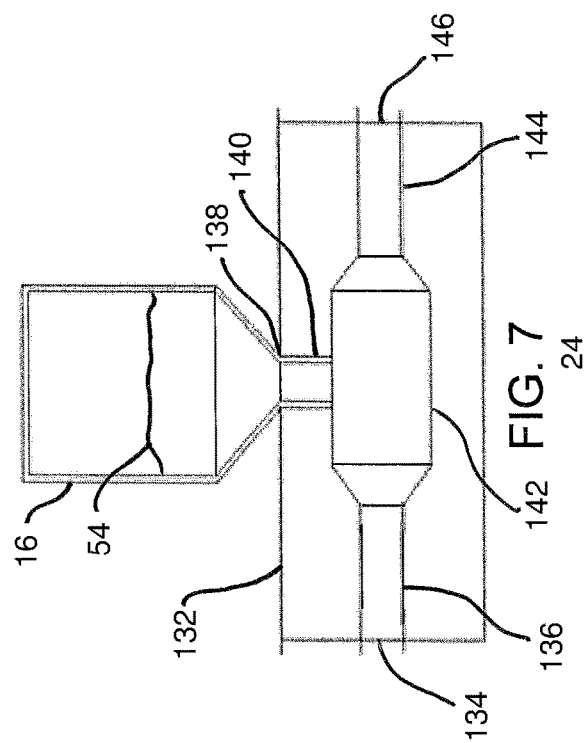

While auger 150 is shown having a length spanning junction 158 and passage 164, it is contemplated that the length may be different. For example, as shown in FIG. 9, an auger 166 may extend across a junction 168, through a passage 170, and into powder chamber 16. It is also contemplated that an auger may extend all the way from a wall of junction 168 furthest from powder chamber 16 to closed end 24 of powder chamber 16, where one end of a shaft of the auger may be rotationally coupled. Alternatively, an auger (not shown) may be entirely contained within junction 158, for example not extending into passage 164.

Figure 10:
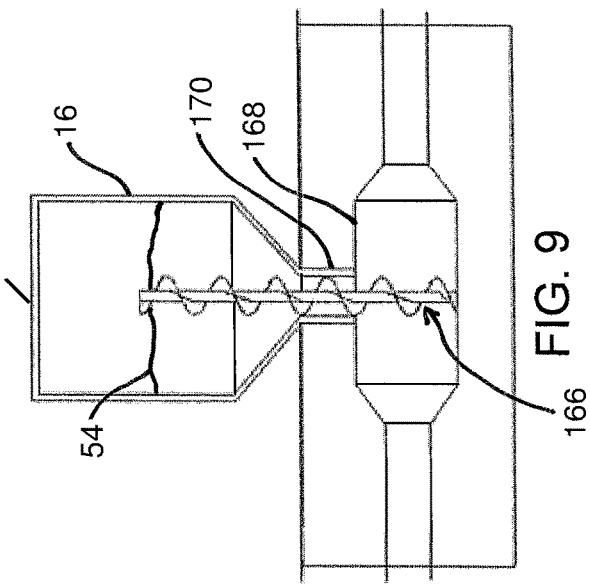
Figure 12:
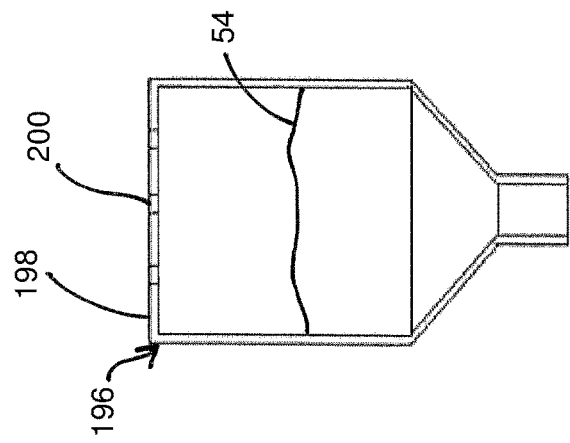
FIGS. 12-16 show powder chambers, in accordance with aspects of the present disclosure.

FIG. 10 shows a mixing chamber 172 including a passage 174 for the pressurized fluid, a junction 176 in which powdered agent 54 may be fluidized by the pressurized fluid, and a passage 178 through which fluidized powdered agent 54 may exit from junction 176. Mixing chamber 172 also may include a passage 180 directly fluidly coupling passage 174 to passage 178. A portion of the pressurized fluid from passage 174 may bypass junction 176 and flow directly into passage 178 via passage 180. In some instances, when bodily fluids or other contaminants enter catheter 18 from distal end 20, they may form a clog or clot within catheter 18 upon coming into contact with fluidized powdered agent 54 within catheter 18. The bodily fluids/contaminants tend to enter distal end 20 when there is nothing flowing out of catheter 18. Passage 180 may ensure that at least some of the pressurized fluid may flow through catheter 18, even if junction 176 becomes clogged, thereby inhibiting additional bodily fluids/contaminants from entering distal end 20. The pressurized fluid also may help expel clogs/clots from within catheter 18.

Mixing chamber 172 also may include a valve assembly 182 that may control the amount of the pressurized fluid that may flow to junction 176 and to passage 180. For example, during normal operation, valve assembly 182 may direct all of the pressurized fluid from passage 174 to junction 176 for fluidizing powdered agent 54. If pressure in junction 176 increases due to clogging therein, valve assembly 182 may direct at least some of the pressurized fluid into passage 180 to keep bodily fluids/contaminants from entering distal end 20 of catheter 18.

Figure 11:
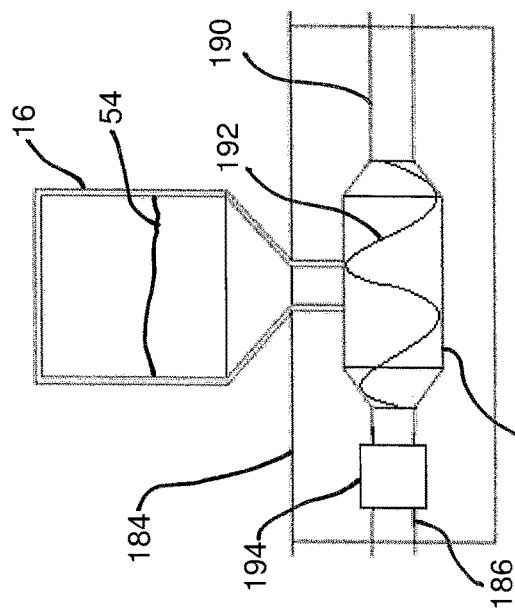

FIG. 11 shows a mixing chamber 184 including a passage 186 for the pressurized fluid, a junction 188 in which powdered agent 54 may be fluidized by the pressurized fluid, and a passage 190 for fluidized powdered agent 54. A curved, wavy, and/or sinusoidal wire 192 may extend within junction 188. In one example, junction 188 may include opposite ends, and wire 192 may extend longitudinally through junction 188 from one of those ends to the other. Wire 192 may vibrate to prevent powdered agent 54 from packing or clogging as it enters junction 188. Wire 192 may vibrate due to forces generated thereon by the pressurized gas, and/or wire 192 may be vibrated by a suitable actuator (not shown). For example, one end of wire 192 may be coupled to the actuator. Alternatively, both ends of wire 192 may be coupled to the actuator. It is contemplated that wire 192 may extend into passage 186 and/or passage 190 to facilitate its vibration and/or to help fluidize the powdered agent 54.

Mixing chamber 184 also may include a valve assembly 194. Valve assembly 194 may be positioned along passage 186. In one example, valve assembly 194 may include a one-way valve that may allow the pressurized gas from passage 186 to flow into junction 188, but may prevent powdered agent 54 from flowing from junction 188 into passage 186. Preventing such backflow may help ensure that gas line 22 and/or the pressurized gas source do not become clogged from exposure to powdered agent 54.

FIGS. 12-16 show examples of powder chambers. It is contemplated that any of the powder chambers may be used in place of any other, including powder chamber 16. It also is contemplated that any aspect of any of the powder chambers may be used in any of the other powder chambers. A powder chamber 196, shown in FIG. 12, may include a closed end 198. Closed end 198 may have at least one aperture 200. During use, vacuum pressure may be generated in powder chamber 196 as powdered agent 54 is drawn out from powder chamber 196. An increase in vacuum pressure in powder chamber 196 may make it more difficult for powdered agent 54 to exit from powder chamber 196. Aperture 200 may allow air to be drawn into powder chamber 196, thereby reducing the vacuum pressure and facilitating the outflow of powdered agent 54. Closed end 198 may include a foil sheet the user can puncture through to make aperture(s) 200. Alternatively, closed end 198 may include preformed aperture(s) 200 covered by a liner (not shown). The liner may be removed by the user to expose aperture(s) 200.

Figure 13:
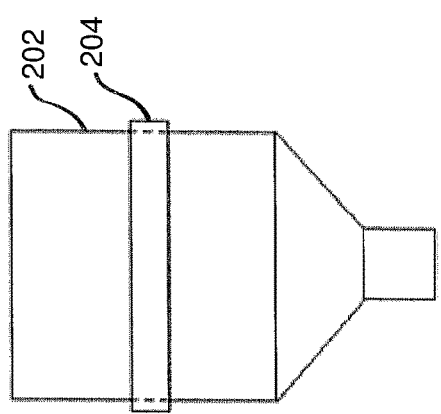

FIG. 13 shows a powder chamber 202 having a vibration ring 204 mounted thereon. When vibration ring 204 is activated by the user, vibration ring 204 may oscillate, thereby shaking powder chamber 202. The shaking may help agitate powdered agent 54 to reduce or eliminate packing or clogging and facilitate the outflow of powdered agent 54 from powder chamber 202. Vibration ring 204 is shown mounted to an outer surface of powder chamber 202, but it is contemplated that vibration ring 204 may be provided within powder chamber 202, or may be embedded in material forming powder chamber 202. It is also contemplated that any suitable vibrating device may be used, even ones not shaped like a ring, to shake powder chamber 202. The vibration may be driven by any suitable mechanical or electromechanical mechanism.

Figure 14:
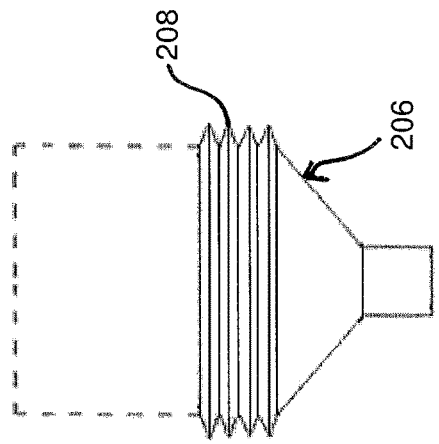

FIG. 14 shows a powder chamber 206. Powder chamber 206 may be collapsible from a first state (shown with dotted lines) to a second state (shown with solid lines). In one example, powder chamber 206 may include bellows 208. The concertinaed arrangement of bellows 208 may allow powder chamber 206 to expand and contract. In another example, powder chamber 206 may be made from a malleable material that may be crushed to a collapsed state. Collapsing powder chamber 206 may exert a force on powdered agent 54 therein that may expel powdered agent 54 from powder chamber 206.

Figure 15:
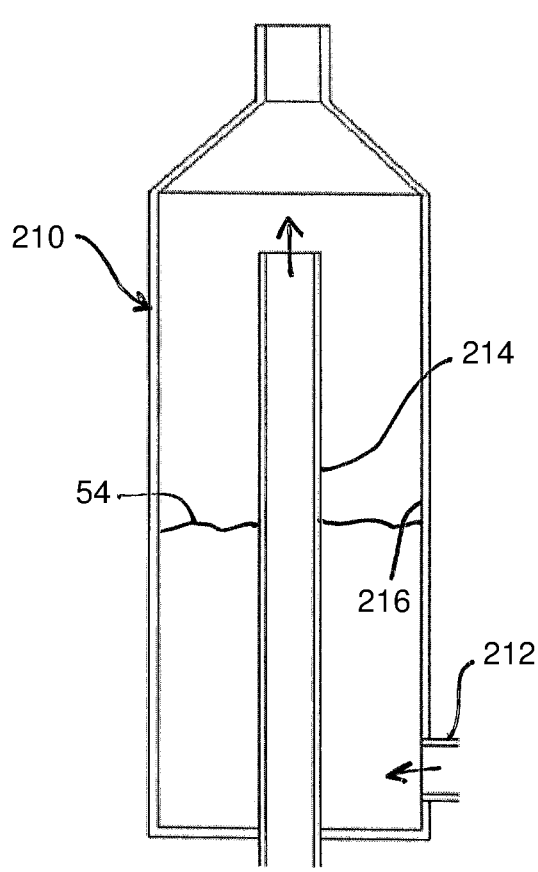
Figure 16:
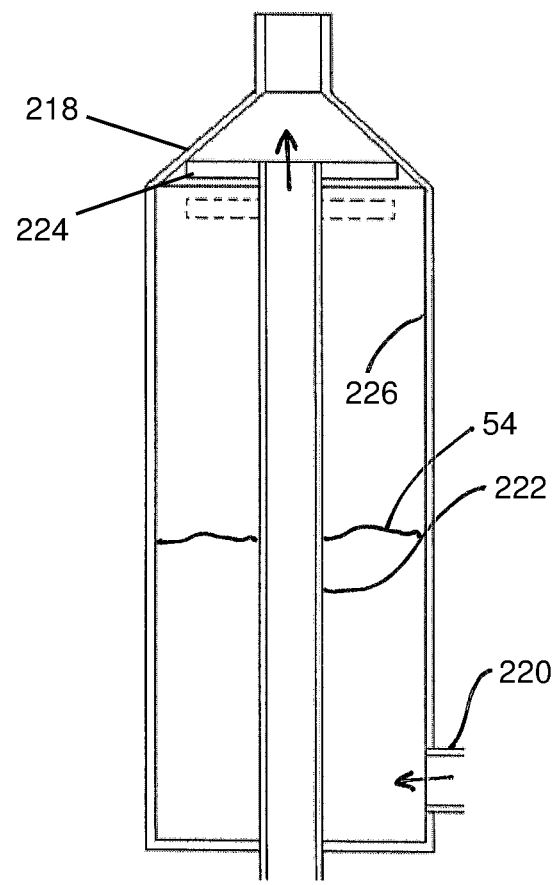

FIG. 15 shows a powder chamber 210. Powder chamber 210 may include a gas line 212 and a gas line 214. In one example, gas line 212 may be fluidly coupled to a wall 216 of powder chamber 210. A central longitudinal axis of gas line 212 may be offset from a central longitudinal axis of powder chamber 210. For example, the central longitudinal axis of gas line 212 may not intersect the central longitudinal axis of powder chamber 210. The pressurized gas expelled from gas line 212 therefore may swirl around within powder chamber 210 along wall 216, creating a swirling vortex of the pressurized gas and powdered agent 54 within powder chamber 210. This movement may reduce or eliminate packing or clogging of powdered agent 54 in powder chamber 210. Gas line 214 may extend into powder chamber 210. A central longitudinal axis of gas line 214 may be coaxial with or parallel to the central longitudinal axis of powder chamber 210. The pressurized gas expelled from gas line 214 may force the swirling powdered agent 54 out of powder chamber 210, moving powdered agent 54 against the force of gravity. In one example, gas line 214 may include one or more side apertures through which the pressurized gas may be expelled, to help clear powder chamber 210. Powder chamber 210 may be mounted to bottoms of mixing chambers and/or chasses, such that powdered agent 54 flows upwardly into the mixing chambers/chasses. Gas line 212 and gas line 214 may receive one or more pressurized gases from any suitable source(s) (not shown).

FIG. 16 shows a powder chamber 218 including a gas line 220 and a gas line 222, similar to gas lines 212 and 214, respectively. A plate or disc 224 may be slidably mounted on gas line 222. Initially, plate 224 may contact a wall 226 of powder chamber 218, thereby blocking powdered agent 54 from exiting powder chamber 218. When the pressurized gas is expelled into powder chamber 218 from gas line 222, the increase in gas pressure in powder chamber 218 may force plate 224 to a retracted state (shown with dashed lines). In the retracted state of plate 224, powdered agent 54 may flow around the edges of plate 224 and out of powder chamber 218. It is contemplated that the pressurized gas from gas line 220 may swirl powdered agent 54 while plate 224 blocks powdered agent 54 from exiting powder chamber 218. The swirled powdered agent 54 may flow out of powder chamber 218 whenever the pressurized gas from gas line 220 creates sufficient gas pressure to force plate 224 away from wall 226, creating a pathway for powdered agent 54 to flow around plate 224.

In some examples where powder chamber 210 and/or powder chamber 218 is used, the pressurized gas(es) emitted therein may be sufficient to fluidize powdered agent 54. This may allow the chassis, to which powder chamber 218 is coupled, to be simplified. For example, the chassis need not include a pressurized gas passage or a mixing/fluidizing junction. Fluidized powdered agent 54 may flow into the chassis from powder chamber 218, and out of the chassis into a catheter for delivery to a site. Alternatively, powder chamber 210 and/or powder chamber 218 may be used in a chassis that also has a pressurized gas passage and a mixing/fluidizing junction, to enhance the fluidization of the powdered agent 54 utilizing two stages of fluidization.

Figure 17:
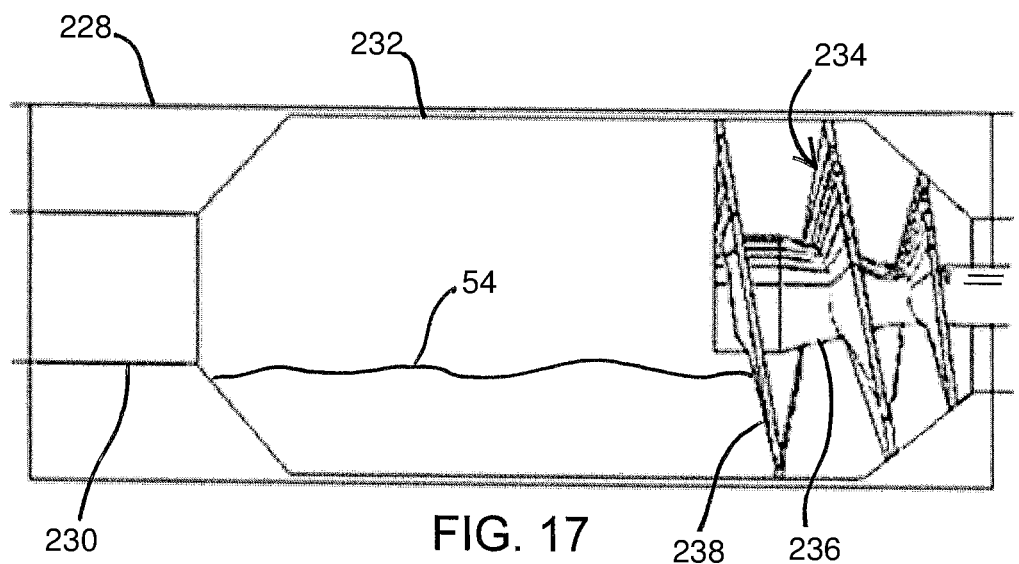
FIG. 17 shows another mixing chamber, in accordance with aspects of the present disclosure.

FIG. 17 shows a mixing chamber 228 including a passage 230 for the pressurized gas, and a passage 232 loaded with powdered agent 54. Powdered agent 54 may be pre-loaded into passage 232, such that a separate powder chamber is not needed. Alternatively, passage 232 may receive powdered agent 54 from a separate powder chamber, as shown in other examples described above. Mixing chamber 228 also may include an auger 234. Auger 234 may be positioned in passage 232. Auger 234 may include a shaft 236 and a helical flange 238 extending longitudinally along shaft 236. Shaft 236 may be rotationally mounted, and may be rotated by an actuator (not shown), such as a manually-operated dial or knob, a motor, a gear assembly, and/or any other suitable actuator. Alternatively, forces generated by the pressurized fluid may cause auger 234 to rotate.

In one example, auger 234 may be positioned at or near a downstream/exit end of passage 232. Shaft 236 may extend longitudinally through passage 232. It is contemplated, for example, that a central longitudinal axis of shaft 236 may be parallel to or coaxial with a central longitudinal axis of passage 232. It also is contemplated that auger 234 may have a width or diameter substantially equal to, or less than, a width or diameter of passage 232. As shown in FIG. 17, the width or diameter of auger 234 may taper going in a downstream direction. The tapering width or diameter may help position edges of helical flange 238 at or near a tapering end of passage 232.

During use, the pressurized gas from passage 230 may enter passage 232, and may fluidize powdered agent 54. The pressurized gas and/or fluidized powdered agent 54 may impinge against auger 234. This impingement may rotate auger 234. Auger 234 may help loosen powdered agent 54, thereby facilitating its fluidization, and/or may help control a rate of delivery of fluidized powdered agent 54 out of mixing chamber 228.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. An apparatus for delivering a powdered agent into a subject's body, the apparatus comprising:
    a powder chamber housing the powdered agent;
    a chassis in fluid connection with the powder chamber, wherein the chassis includes:
        a first passage for receiving a pressurized gas,
        a second passage including a non-tapered region and a tapered region, the non-tapered region is configured for receiving the powdered agent from the powder chamber,
        a junction in fluid communication with the first passage and the second passage, wherein at least a first portion of the pressurized gas is introduced into the powdered agent at the junction to mix with the powdered agent,
        the tapered region is positioned downstream of the non-tapered region and upstream of the junction, wherein at least a portion of the powdered agent received in the non-tapered region of the second passage from the powder chamber is positioned along the tapered region;
        a third passage in fluid communication with the first passage at a first end of the third passage, and in fluid communication with the second passage via the tapered region at a second end of the third passage that is opposite of the first end, wherein the third passage is configured to direct a second portion of the pressurized gas from the first passage into the tapered region, and an angle of the third passage relative to the tapered region causes the second portion of the pressurized gas to be emitted tangentially relative to a wall of the tapered region to create a vortex of the second portion of the pressurized gas and the powdered agent in the second passage;
    wherein the chassis is configured to:
        (i) direct the portion of the powdered agent positioned in the tapered region into the non-tapered region in response to receiving the second portion of the pressurized gas;
        (ii) agitate the powdered agent within the non-tapered region; and
        (iii) direct the agitated powdered agent from the non-tapered region downstream through the tapered region and into the junction, and
    a fourth passage in fluid communication with the junction, wherein the fourth passage receives the agitated powdered agent from the junction for exiting the chassis.

2. The apparatus of claim 1, wherein the powder chamber is positioned above the chassis, such that gravity assists movement of the powdered agent out of the powder chamber and into the non-tapered region of the second passage.

3. The apparatus of claim 1, wherein the first passage, the junction, and the fourth passage are substantially aligned.

4. The apparatus of claim 1, wherein a central longitudinal axis of the second passage is substantially perpendicular to a central longitudinal axis of at least one of the first passage or the fourth passage.

5. The apparatus of claim 1, wherein an opening is formed in a wall of the tapered region where the third passage meets the tapered region.

6. The apparatus of claim 1, wherein the non-tapered region has a first width and the second passage includes a second non-tapered region having a second width that is smaller than the first width.

7. The apparatus of claim 1, further including an agitation mechanism coupled to the powder chamber, wherein the agitation mechanism is configured to agitate the powdered agent stored within the powder chamber to inhibit clogging or packing of the powdered agent within the powder chamber.

8. The apparatus of claim 6, wherein the first width is constant along a first length of the non-tapered region, and the second width is constant along a second length of the second non-tapered region.

9. The apparatus of claim 6, wherein the tapered region is positioned between the non-tapered region and the second non-tapered region.

10. The apparatus of claim 9, wherein the tapered region has a third width that varies along a length of the tapered region.

11. The apparatus of claim 10, wherein the third width is greater along a portion adjacent to the non-tapered region relative to another portion adjacent to the second non-tapered region.

12. The apparatus of claim 10, wherein the tapered region defines a funnel that is configured to facilitate outflow of the powdered agent from the second passage to the junction.

13. The apparatus of claim 12, wherein the funnel is configured to inhibit clogging or packing of the powdered agent within the second passage.

14. The apparatus of claim 7, wherein the agitation mechanism includes a vibration ring that is configured to oscillate and vibrate the powder chamber.

15. An apparatus for delivering a powdered agent into a subject's body, the apparatus comprising:
- a powder chamber housing the powdered agent;
- a chassis fluidly coupled to the powder chamber, wherein the chassis includes:
  - a first passage for receiving pressurized gas from a pressurized gas source;
  - a second passage including a non-tapered region and a tapered region, the non-tapered region is configured for receiving the powdered agent from the powder chamber;
  - the tapered region for receiving at least a portion of the powdered agent received in the non-tapered region from the powder chamber;
  - a third passage in fluid communication with the first passage, the tapered region, and the non-tapered region through the tapered region, the third passage for directing the pressurized gas from the first passage into the tapered region,
  - wherein an angle of the third passage relative to the tapered region causes the pressurized gas to be emitted tangentially relative to a wall of the tapered region to create a vortex of the pressurized gas and the powdered agent in the second passage;
  - wherein the chassis is configured to (i) direct the portion of the powdered agent received on the tapered region into the non-tapered region, (ii) agitate the powdered agent in the tapered region and the non-tapered region of the second passage, and (iii) direct to the agitated powdered agent from the non-tapered region of the second passage downstream through the tapered region; and
- a fourth passage for receiving the agitated powdered agent from the second passage and directing the agitated powdered agent out of the apparatus.

16. The apparatus of claim 15, wherein the second passage includes a second non-tapered region, wherein the tapered region is positioned between the non-tapered region and the second non-tapered region.

17. The apparatus of claim 16, wherein the non-tapered region has a first width that is constant, the second non-tapered region has a second width that is constant and smaller than the first width, and the tapered region has a third width that is tapered toward the second non-tapered region such that the third width is greater along a portion of the tapered region adjacent to the non-tapered region relative to another portion adjacent to the second non-tapered region.

18. An apparatus for delivering a powdered agent into a subject's body, the apparatus comprising:
- a powder chamber housing the powdered agent;
- a chassis in fluid communication with the powder chamber and a pressurized gas source, the chassis including:
  - a first passage for receiving pressurized gas from the pressurized gas source;
  - a second passage including a non-tapered region and a tapered region, the non-tapered region is configured for receiving the powdered agent from the powder chamber;
  - the tapered region for receiving at least a portion of the powdered agent received in the non-tapered region of the second passage from the powder chamber;
  - a third passage for directing the pressurized gas from the first passage into the second passage via the tapered region, wherein an angle of the third passage relative to the tapered region causes the pressurized gas to be emitted tangentially relative to a wall of the tapered region to create a vortex of the pressurized gas and the powdered agent in the second passage;
- wherein the chassis is configured to:
  - (i) move the portion of the powdered agent received in the tapered region into the non-tapered region of the second passage;
  - (ii) agitate the powdered agent in the non-tapered region of the second passage; and
  - (iii) direct the agitated powdered agent from the non-tapered region of the second passage and through the tapered region; and
- a fourth passage for receiving the agitated powdered agent from the second passage via the tapered region for delivery to the subject's body.

* * * * *